(12) United States Patent
Mujwid et al.

(10) Patent No.: US 11,399,944 B2
(45) Date of Patent: Aug. 2, 2022

(54) INFLATABLE PENILE PROSTHESIS HAVING A CYLINDER WITH A POROUS PORTION

(71) Applicant: Boston Scientific Scimed, Inc., Maple Grove, MN (US)

(72) Inventors: James Ryan Mujwid, Hudson, WI (US); Jessica Elizabeth Felton, Minneapolis, MN (US); Ryan Earl Fredrick, Eden Prairie, MN (US); Thomas Andrew Albrecht, Edina, MN (US); John Anders Bostrom, Saint Paul, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 288 days.

(21) Appl. No.: 16/374,238

(22) Filed: Apr. 3, 2019

(65) Prior Publication Data
US 2019/0307565 A1 Oct. 10, 2019

Related U.S. Application Data

(60) Provisional application No. 62/655,378, filed on Apr. 10, 2018.

(51) Int. Cl.
*A61F 2/26* (2006.01)

(52) U.S. Cl.
CPC ........ *A61F 2/26* (2013.01); *A61F 2230/0069* (2013.01); *A61F 2240/001* (2013.01); *A61F 2250/0013* (2013.01)

(58) Field of Classification Search
CPC ............................. A61F 2/26; A61F 2240/001
See application file for complete search history.

(56) References Cited

U.S. PATENT DOCUMENTS

| 5,669,870 A | 9/1997 | Elist |
| 5,899,849 A | 5/1999 | Elist et al. |
| 2005/0014993 A1 | 1/2005 | Mische et al. |
| 2009/0132043 A1* | 5/2009 | George ..................... A61F 2/26 623/11.11 |
| 2018/0318085 A1* | 11/2018 | Felton ....................... A61F 2/26 |

FOREIGN PATENT DOCUMENTS

| EP | 1820473 A1 | 8/2007 |
| WO | 2013096615 A1 | 6/2013 |

OTHER PUBLICATIONS

International Search Report and Written Opinion for Application No. PCT/US2019/025797, dated Sep. 17, 2019, 19 pages.

\* cited by examiner

*Primary Examiner* — John P Lacyk
(74) *Attorney, Agent, or Firm* — Brake Hughes Bellermann LLP

(57) ABSTRACT

According to an aspect, an implant includes an inflatable member and a pump assembly configured to facilitate a transfer of a fluid from the reservoir to the inflatable member. The inflatable member has a sidewall that defines a lumen and a porous structure disposed within the lumen.

20 Claims, 9 Drawing Sheets

INFLATABLE PENILE PROSTHESIS HAVING A CYLINDER WITH A POROUS PORTION

CROSS-REFERENCE TO RELATED APPLICATION

This application is a Nonprovisional of, and claims priority to, U.S. Patent Application No. 62/655,378, filed on Apr. 10, 2018, entitled "INFLATABLE PENILE PROSTHESIS HAVING A CYLINDER WITH A POROUS PORTION", which is incorporated by reference herein in its entirety.

TECHNICAL FIELD

This disclosure relates generally to bodily implants and more specifically to bodily implants, such as penile prostheses that include inflatable members.

BACKGROUND

One treatment for male erectile dysfunction is the implantation of a penile prosthesis that mechanically erects the penis. Some existing penile prostheses include inflatable cylinders or members that can be inflated or deflated using a pump mechanism. In some existing devices, the inflatable cylinder or member requires a relatively large amount of force to inflate. Additionally, in some existing devices, the pump mechanism may require many sequential squeezes or activations to inflate the cylinder or member. Furthermore, in some existing devices, the inflatable cylinder or member may assume a flat, unnatural shape when in a deflated configuration.

Accordingly, it would be useful to provide a bodily implant, such as a penile prosthesis, that includes an improved cylinder or member that can be more easily inflated. Additionally, it would be useful to provide a bodily implant, such as a penile prosthesis, that includes an inflatable cylinder or member that may assume a natural shape when in the deflated configuration.

SUMMARY

According to an aspect, an implant includes an inflatable member and a pump assembly configured to facilitate a transfer of a fluid from the reservoir to the inflatable member. The inflatable member has a sidewall that defines a lumen and a porous structure disposed within the lumen.

In some embodiments, the porous structure defines a plurality of cavities. In some embodiments, the inflatable member defines a longitudinal axis, the porous structure extends along the longitudinal axis. In some embodiments, the sidewall includes an outer surface, the outer surface of the sidewall is substantially smooth.

In some embodiments, the inflatable member is configured to be placed in an inflated configuration and a deflated configuration. In some embodiments, the inflatable member is configured to be placed in an inflated configuration and a deflated configuration, the inflatable member having a tubular shape when in the deflated configuration. In some embodiments, the inflatable member is configured to be placed in an inflated configuration and a deflated configuration, the inflatable member having a tubular shape when in the inflated configuration. In some embodiments, the inflatable member is configured to be placed in an inflated configuration and a deflated configuration, the inflatable member having a tubular shape when in the deflated configuration and having a tubular shape when in the inflated configuration.

In some embodiments, the inflatable member is configured to be placed in an inflated configuration and a deflated configuration, the inflatable member configured to extend along a longitudinal axis of the inflatable member when placed in the inflated configuration. In some embodiments, the inflatable member is configured to be placed in an inflated configuration and a deflated configuration, the inflatable member configured to extend in a direction transverse to a longitudinal axis of the inflatable member when placed in the inflated configuration.

In some embodiments, the porous structure defines a plurality of cavities, the fluid being configured to be disposed within the plurality of cavities when the inflatable member is placed in an inflated configuration.

In some embodiments, the implant includes a first cap coupled to a first end portion of the sidewall and a second cap coupled to a second end portion of the sidewall.

In some embodiments, the implant includes a first cap coupled to a first end portion of the sidewall and a second cap coupled to a second end portion of the sidewall. The porous structure being disposed between the first cap and the second cap.

In some embodiments, the implant includes a reservoir configured to retain the fluid, and the pump is configured to help facilitate a transfer of the fluid from the reservoir to the inflatable member when the implant is in an inflation mode.

In some embodiments, the pump assembly includes a valve body and a pump bulb member.

According to another aspect, a method, includes disposing a first material within a lumen of a sheath; disposing a second material within the lumen of the sheath, the second material being different than the first material; and removing the first material from with lumen of the sheath while leaving the second material disposed within the sheath.

In some embodiments, the first material is water-soluble, the second material is non-soluble in water. In some embodiments, the removing the first material from the lumen includes passing a liquid through the lumen of the sheath.

In some embodiments, the second material is disposed within the lumen of the sheath after the first material is disposed within the sheath.

In some embodiments, the method includes disposing tubular members within the lumen of the sheath.

DETAILED DESCRIPTION

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the present disclosure.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "moveably coupled," as used herein, is defined as connected, although not necessarily directly and mechanically.

In general, the embodiments are directed to medical devices such as penile prostheses or other bodily implants. The term patient or user may hereafter be used for a person who benefits from the medical device or the methods disclosed in the present disclosure. For example, the patient can be a person whose body is implanted with the medical device or the method disclosed for operating the medical device by the present disclosure. For example, in some embodiments, the patient may be a human male, a human female, or any other mammal.

The embodiments discussed herein may improve the performance of an inflatable member of the device. For example, the inflatable member may have improved stiffness or rigidity, improved reliability, or improved deflation or inflation times. In some embodiments, inflating the inflatable member may be facilitated by requiring less force, less pressure, or less fluid transfer to inflate the inflatable member. Additionally, in some embodiments, the inflatable member may retain or maintain a tubular shape when the inflatable member is placed in its deflated configuration.

The embodiments may include an inflatable penile prosthesis having a pump assembly, an inflatable member, and a reservoir. The inflatable member may be implanted into the corpus cavernosae of a patient or user, the reservoir may be implanted in the user's abdomen, and the pump assembly may be implanted in the scrotum. The pump assembly may switch between an inflation position and a deflation position such that a user can operate the device to place the inflatable penile prosthesis in either an inflation mode to transfer fluid from the reservoir to the inflatable member or a deflation mode to transfer the fluid from the inflatable member back to the reservoir.

Figure 1:
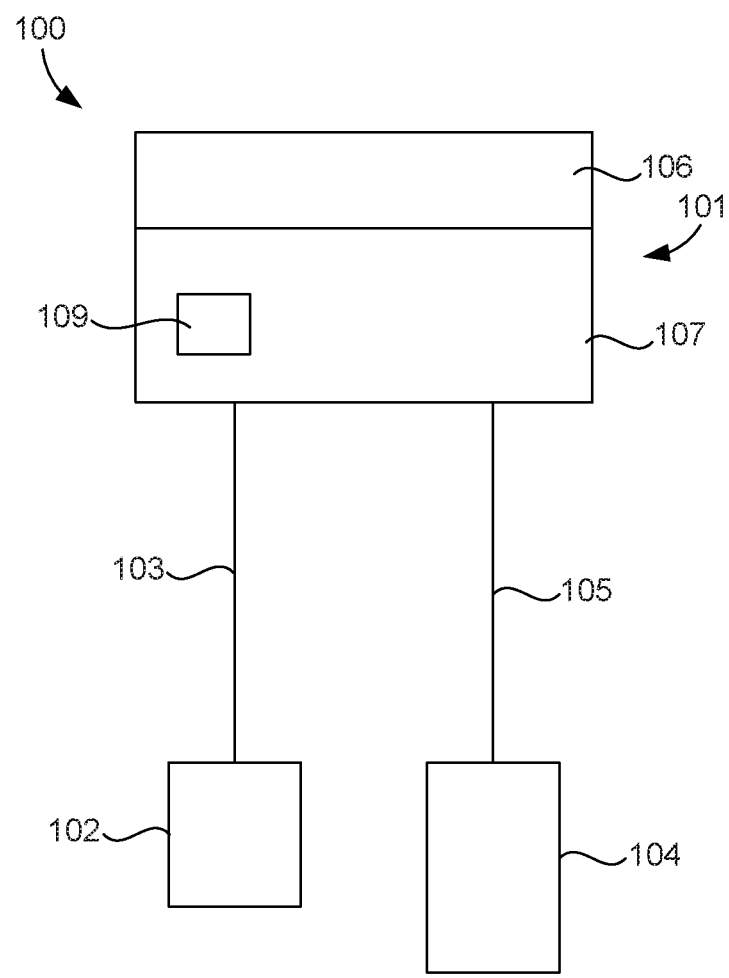
FIG. 1 schematically illustrates a penile prosthesis according to an embodiment.

FIG. 1 schematically illustrates an inflatable penile prosthesis 100 according to an aspect. The inflatable penile prosthesis 100 may include a reservoir 102, a cylinder or inflatable member 104, and a pump assembly 101 configured to transfer fluid between the reservoir 102 and the inflatable member 104. In some examples, the inflatable member 104 may be implanted into the corpus cavernosae of the user, the reservoir 102 may be implanted in the abdomen or pelvic cavity of the user (e.g., the reservoir 102 may be implanted in the lower portion of the user's abdominal cavity or the upper portion of the user's pelvic cavity), and the pump assembly 101 may be implanted in the scrotum of the user.

The inflatable member 104 may be capable of expanding upon the injection of fluid into a cavity of the inflatable member 104. For instance, upon injection of the fluid into the inflatable member 104, the inflatable member 104 may increase its length and/or width, as well as increase its rigidity. In some examples, the inflatable member 104 may include a pair of cylinders or at least two cylinders, e.g., a first cylinder member and a second cylinder member. The volumetric capacity of the inflatable member 104 may depend on the size of the cylinders. In some examples, the volume of fluid in each cylinder may vary from about 10 milliliters in smaller cylinders and to about 50 milliliters in larger sizes. In some examples, the first cylinder member may be larger than the second cylinder member. In other examples, the first cylinder member may have the same size as the second cylinder member.

In some embodiments, the inflatable member 104 or cylinder includes a sidewall, an outer sheath or tubular member and an internal structural member. In some embodiments, the outer sheath or tubular member of the inflatable member 104 defines a lumen and the structural member is disposed within the lumen.

In some embodiments, the structural member is porous such that it is configured to allow a fluid to pass through it. In some embodiments, the structural member defines a series or a plurality of cavities and/or channels. In some embodiments, the structural member includes a sponge-like structure.

In some embodiments, the inflatable member 104 includes end caps or end tip members. The end tip members may be coupled to the end portions of the outer sheath. In some embodiments, the structural member is disposed within the lumen defined by the outer sheath and is disposed between the end caps or end tip members.

In some embodiments, the structural member may allow the inflatable member to be inflated at a relatively low pressure. In some embodiments, this may allow the user to inflate the inflatable member 104 with less pumps or activations of the pump or may allow the user to apply less force to the pump to inflate the inflatable member 104. Details of the pump assembly 101 are described below. Additionally, in some embodiments, the structural member of the inflatable member 104 may allow the inflatable member 104 to retain or maintain a tubular shape (or a more anatomically correct shape) when the inflatable member 104 is in its deflated configuration.

The reservoir 102 may include a container having an internal chamber configured to hold or house fluid that is used to inflate the inflatable member 104. The volumetric capacity of the reservoir 102 may vary depending on the size of the inflatable penile prosthesis 100. In some examples, the volumetric capacity of the reservoir 102 may be 3 to 150 cubic centimeters. In some examples, the reservoir 102 is constructed from the same material as the inflatable member 104. In other examples, the reservoir 102 is constructed from a different material than the inflatable member 104.

The inflatable penile prosthesis 100 may include a first conduit connector 103 and a second conduit connector 105. Each of the first conduit connector 103 and the second conduit connector 105 may define a lumen configured to transfer the fluid to and from the pump assembly 101. The first conduit connector 103 may be coupled to the pump assembly 101 and the reservoir 102 such that fluid can be transferred between the pump assembly 101 and the reservoir 102 via the first conduit connector 103. For example, the first conduit connector 103 may define a first lumen configured to transfer fluid between the pump assembly 101 and the reservoir 102. The first conduit connector 103 may include a single or multiple tube members for transferring the fluid between the pump assembly 101 and the reservoir 102.

The second conduit connector 105 may be coupled to the pump assembly 101 and the inflatable member 104 such that fluid can be transferred between the pump assembly 101 and the inflatable member 104 via the second conduit connector 105. For example, the second conduit connector 105 may define a second lumen configured to transfer fluid between the pump assembly 101 and the inflatable member 104. The second conduit connector 105 may include a single or multiple tube members for transferring the fluid between the pump assembly 101 and the inflatable member 104. In some examples, the first conduit connector 103 and the second conduit connector 105 may include a silicone rubber material.

The pump assembly 101 may switch between an inflation mode in which the fluid in the reservoir 102 is transferred to the inflatable member 104 through the pump assembly 101 in a first direction (e.g., inflation direction) and a deflation mode in which the fluid in the inflatable member 104 is transferred back to the reservoir 102 through the pump assembly 101 in a second direction (e.g., deflation direction).

The pump assembly 101 includes a pump (also referred to as a pump bulb member) 106 and a valve body 107. The valve body 107 also includes a selection member 109. The selection member 109 may be used to select or change the mode in which the pump assembly is in. For example, the selection member 109 may be moved from a first position to a second position to place the device in its deflation mode. The selection member 109 may then be moved back to its first position to place the device in its inflation mode. In some embodiments, the selection member 109 is movable with respect to the valve body 107. For example, in some embodiments, the selection member 109 is slidably coupled or slideable with respect to the valve body 107.

The pump 106 may be squeezed or depressed by the user in order to facilitate the transfer of fluid from the reservoir 102 to the inflatable member 104. For example, in the inflation mode, while the user is operating the pump 106, the pump 106 may receive the fluid from the reservoir 102, and then output the fluid to the inflatable member 104. When the user switches to the deflation mode, at least some of the fluid can automatically be transferred back to the reservoir 102 (due to the difference in pressure from the inflatable member 104 to the reservoir 102). Then, the user may squeeze the inflatable member 104 to facilitate the further transfer of fluid through the pump 106 to the reservoir 102.

In some examples, the pump 106 may include a flexible member defining a cavity. In some examples, the pump 106 may define a pump shell having a flexible bulb and a valve body connector, where the valve body connector is designed to fit at least partially over the valve body 107. In some examples, the pump 106 may include a squeeze pump. In some examples, the pump 106 may include a portion that is round or substantially round. In some examples, the pump 106 may include ribbing or dimples to aid the user in gripping the pump 106. The pump 106 may use suction and pressure to move the fluid in and out of the cavity of the pump 106 in the inflation mode. For example, the user may depress or squeeze the pump 106 to expel the fluid out of the cavity, and, when the flexible member returns to its original shape, the resulting suction pushes the fluid into the cavity of the pump 106. In some examples, the pump 106 may have a bulb spring rate that is designed to refill the pump 106 in a selected time frame.

As discussed above, the selection member 109 may be used to select or change the mode in which the pump assembly is in. For example, in one embodiment, the selection member 109 may be placed in the inflate position and the user may then operate the pump 106 to inflate the inflatable member 104 (i.e., move the fluid from the reservoir 102 to the inflatable member 104). For example, the user may repeatedly depress or squeeze the pump 106 until the desired rigidity is achieved.

In some examples, if the reservoir 102 is at least partially pressurized, the fluid may automatically flow out of the reservoir 102 and into the inflatable member 104 without the user depressing or squeezing the pump 106 until the pressure is at least partially equalized between the reservoir 102 and the inflatable member 104.

Then, when the user wants to deflate the inflatable member 104, the user moves selection member 109 to its deflated position. The user may then operate the pump 106 to deflate the inflatable member 104 (i.e., move the fluid from the inflatable member 104 to the reservoir 102). The pump 106 may then return to its original form, which provides a suction force causing fluid to be drawn into the pump 106 from the inflation member 104. The fluid from the inflation member 104 fills the pump 106 (or at least partially fills the pump 106). This pump cycle is repeated until the inflatable member 104 is deflated.

In some examples, the fluid may automatically (upon movement of the selection member 109 to its deflate position) flow out of the inflatable member 104 and into the reservoir 102 without the user depressing or squeezing the pump 106 until the pressure is at least partially equalized between the reservoir 102 and the inflatable member 104.

In some examples, after the inflation member 104 has been deflated, the pump 106 may be squeezed to place the pump in a contracted position or configuration.

Figure 2:
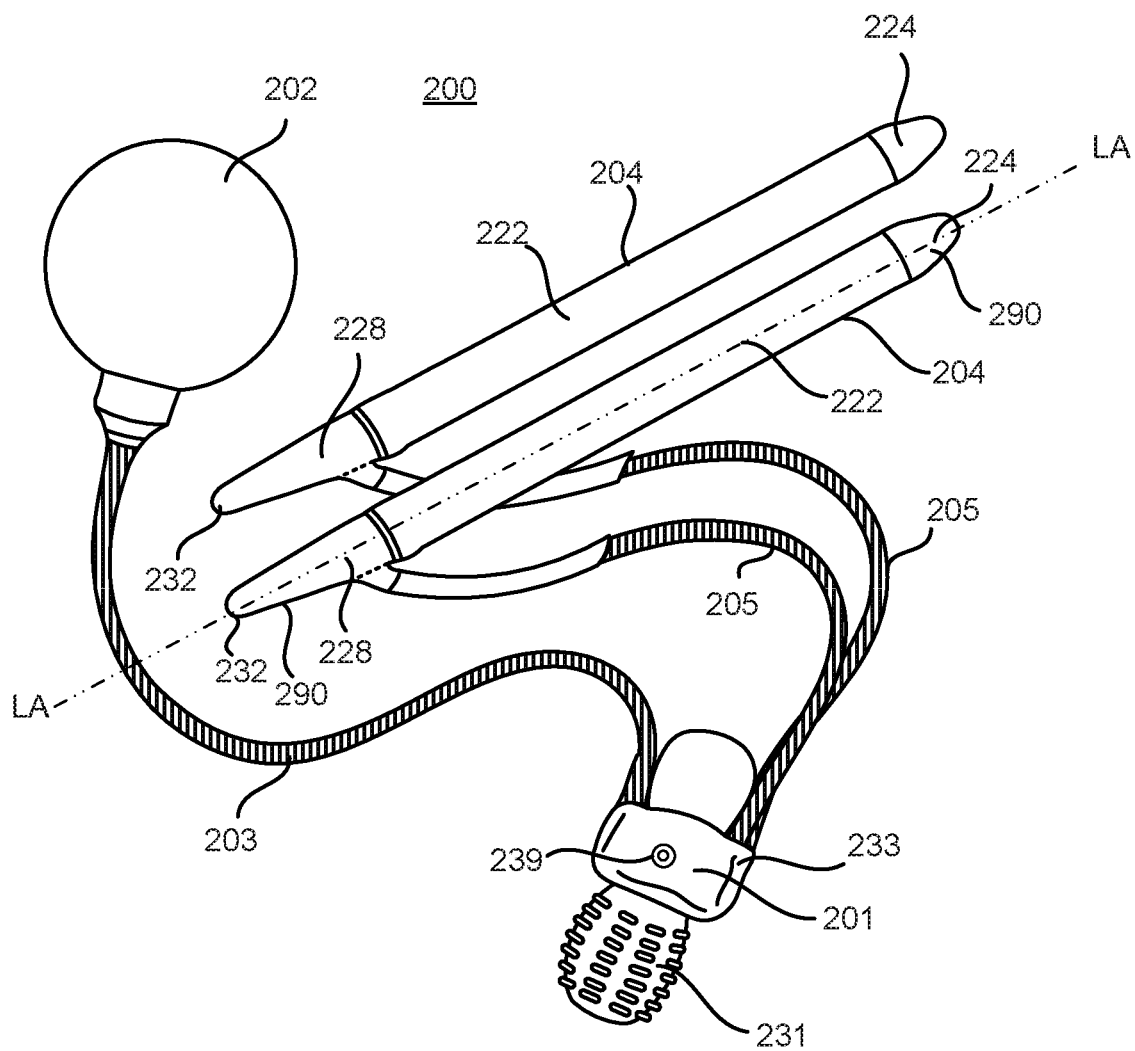
FIG. 2 illustrates a penile prosthesis according to another embodiment.
Figure 3:
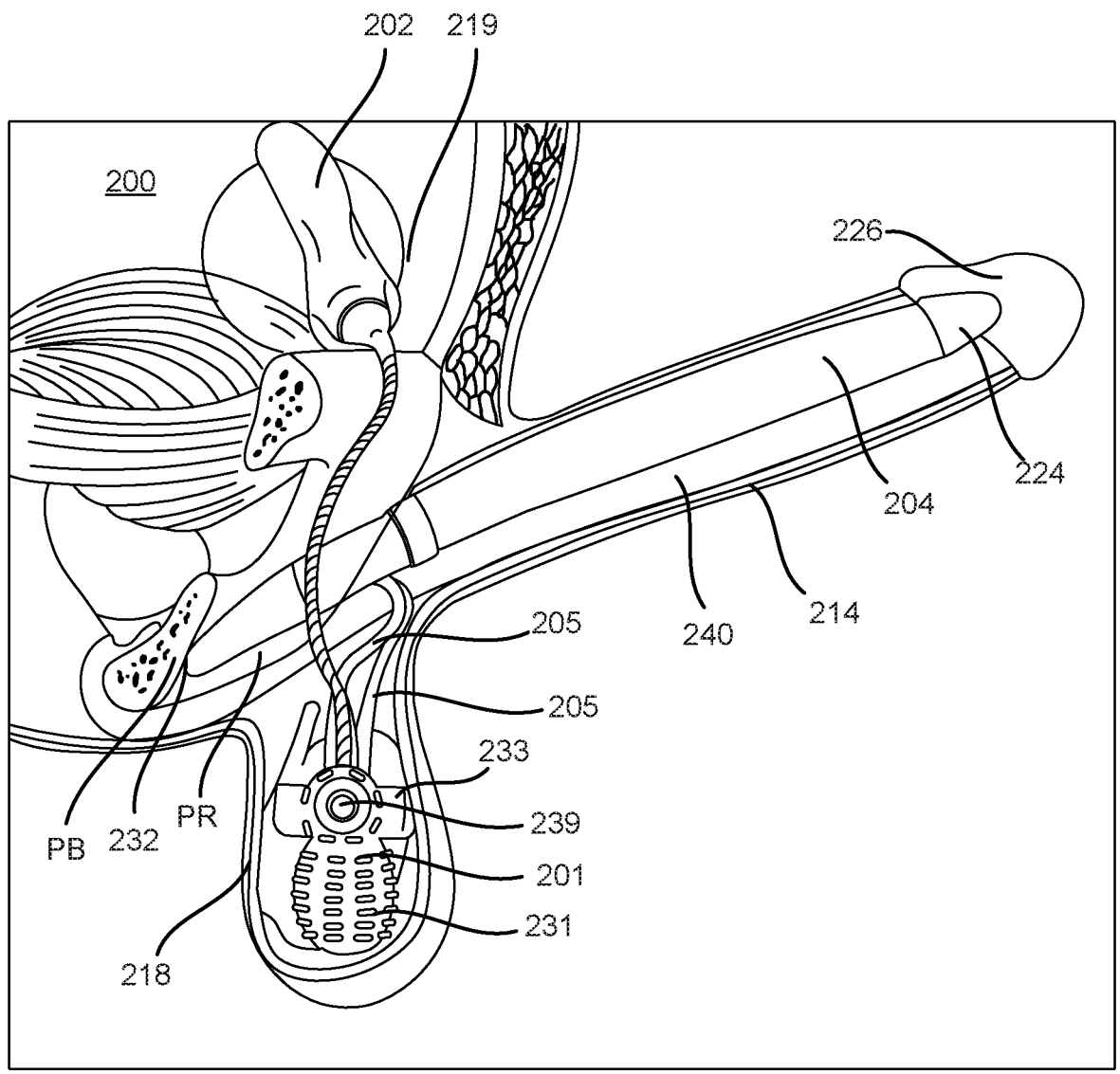
FIG. 3 illustrates the penile prosthesis of FIG. 2 implanted within a patient according to an embodiment.

FIG. 2 illustrates a penile prosthesis 200 according to an aspect. FIG. 3 schematically illustrates the penile prosthesis 200 placed within a body of the user or patient.

The penile prosthesis 200 may include a pair of cylinders 204, and the pair of cylinders or inflatable members 204 are implanted in a penis 214. For example, one of the cylinders 204 may be disposed on one side of the penis 214. The other cylinder 204 (not shown in FIG. 3) of the pair of cylinders may be disposed on the other side of the penis 214. The cylinder 204 may include a second end portion 224, a cavity or inflation chamber 222, and a first end portion 228 having a rear tip 232.

The penile prosthesis 200 may include a pump assembly 201, which may be implanted into the patient's scrotum 218. A pair of conduit connectors 205 may attach the pump assembly 201 to the pair of inflatable members or cylinders 204 such that the pump assembly 201 is in fluid communication with the pair of inflatable members or cylinders 204. Also, the pump assembly 201 may be in fluid communication with a reservoir 202 via a conduit connector 203. The reservoir 202 may be implanted into the user's abdomen 219. The inflation chamber or portion 222 of the cylinder 204 may be disposed within the penis 214. The second end portion 224 of the cylinder 204 may be at least partially disposed within the crown portion 226 or glands of the penis 214. The first end portion 228 may be implanted into the patient's pubic region PR with the rear tip 232 proximate the pubic bone PB.

In order to implant the inflatable members or cylinders 204, the surgeon first prepares the patient. The surgeon often makes an incision in the penoscrotal region, e.g., where the base of the penis 214 meets with the top of the scrotum 218. From the penoscrotal incision, the surgeon may dilate the patient's corpus cavernosae 240 to prepare the patient to receive the pair of inflatable members or cylinders 204. The corpus cavernosum is one of two parallel columns of erectile tissue forming the dorsal part of the body of the penis 214, e.g., two slender columns that extend substantially the length of the penis 214. The surgeon will also dilate two regions of the pubic area (first corpora cavernosae) to prepare the patient to receive the first end portion 228. The surgeon may measure the length of the first and second corpora cavernosae from the incision and the dilated region of the pubic area to determine an appropriate size of the inflatable members or cylinders 204 to implant.

After the patient is prepared, the penile prosthesis 200 is implanted into the patient. The second tip of the second end portion 224 of each cylinder 204 may be attached to a suture. The other end of the suture may be attached to a needle member (e.g., Keith needle). The needle member is inserted into the incision and into the dilated corpus cavernosum. The needle member is then forced through the crown or glands of the penis 226. The surgeon tugs on the suture to pull the cylinder 204 into the corpus cavernosum. This is done for each cylinder of the pair of cylinders 204. Once the inflation chamber 222 is in place, the surgeon may remove the suture from the second tip. The surgeon then inserts the first end portion 228. The surgeon inserts the rear end of the cylinder 204 into the incision and forces the first end portion 228 toward the pubic bone PB until each cylinder 204 is in place.

In the illustrated embodiment, each of the inflatable members or cylinders 204 is structurally and functionally similar. Accordingly, only one of the inflatable members or cylinders will be discussed in detail.

Figure 4:
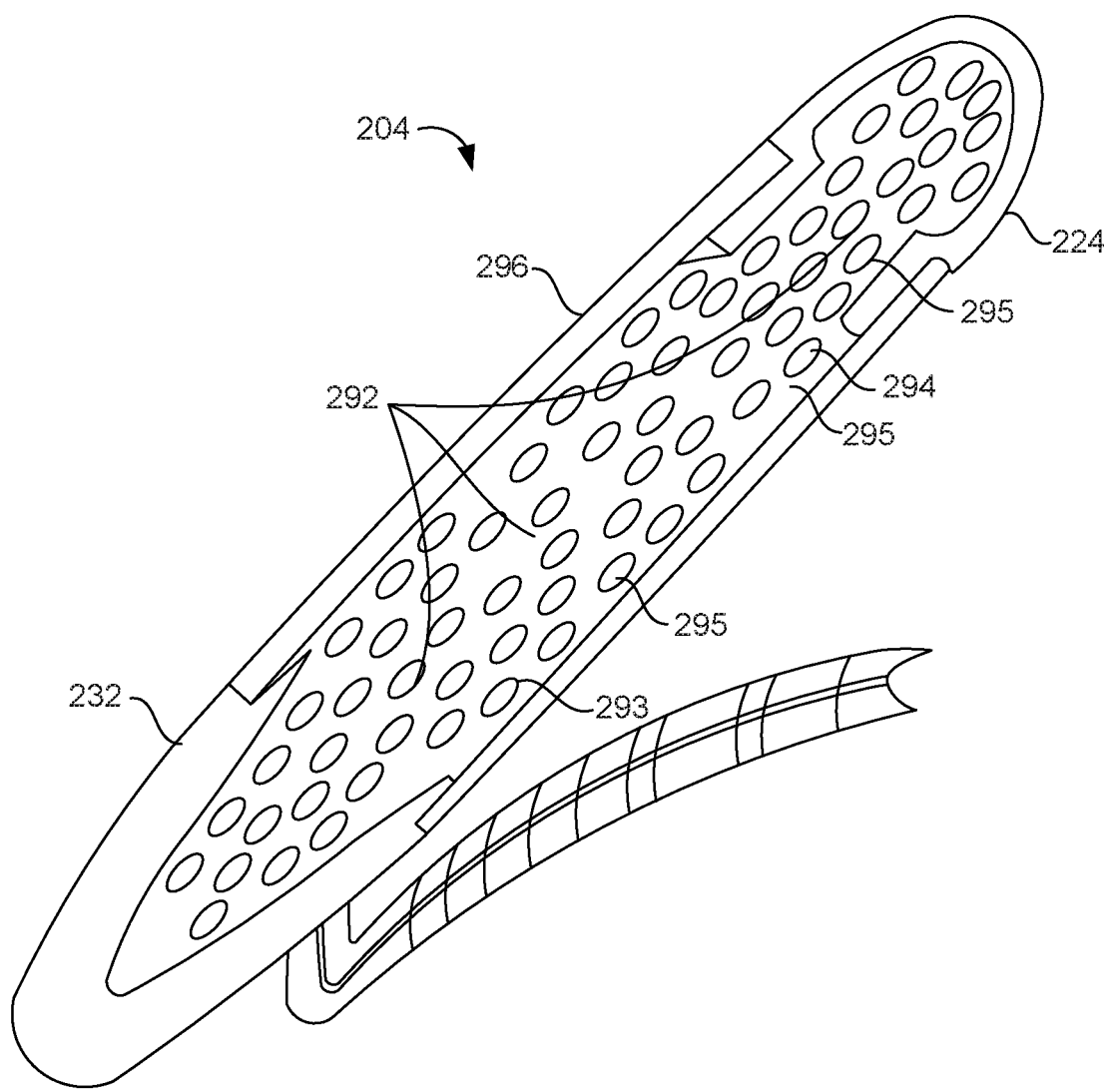
FIG. 4 is a cross-sectional view of the cylinder or inflatable member of the penile prosthesis of FIG. 2.
Figure 5:
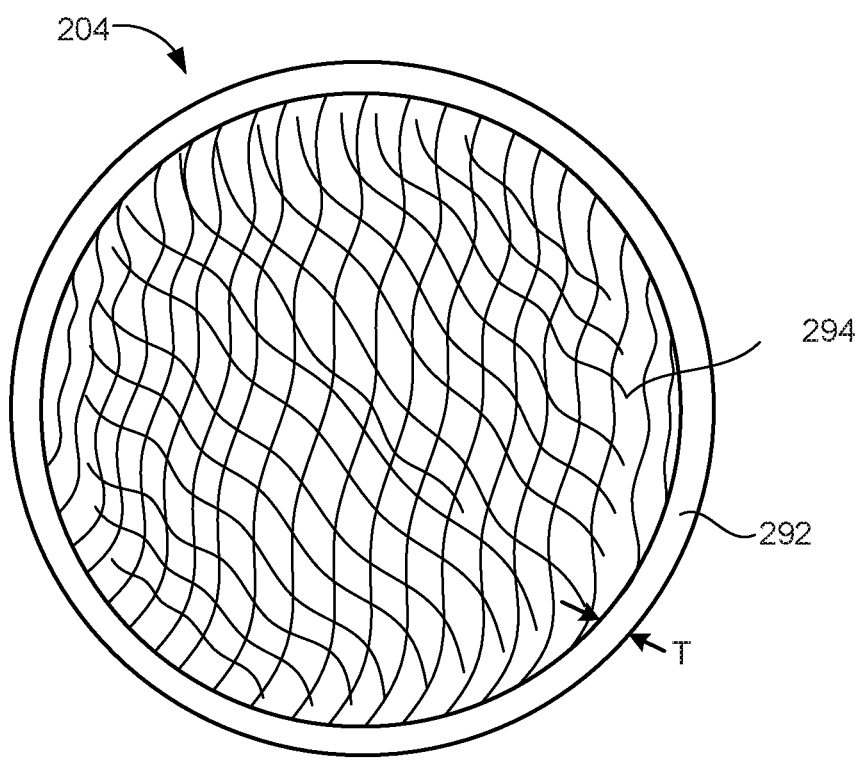
FIG. 5 is an end view of the cylinder or inflatable member of the penile prosthesis of FIG. 2.

FIG. 4 is a cross-sectional view of the cylinder or inflatable member 204. FIG. 5 is an end view of the cylinder or inflatable member 204.

The inflatable member 204 may be capable of expanding upon the injection of fluid into a cavity of the inflatable member 204. For instance, upon injection of the fluid into the inflatable member 204, the inflatable member 204 may increase its length and/or width, as well as increase its rigidity. The volumetric capacity of the inflatable member 204 may depend on the size of the cylinders. In some examples, the volume of fluid in each cylinder may vary from about 10 milliliters in smaller cylinders and to about 50 milliliters in larger sizes.

In the illustrated embodiment, the inflatable member or cylinder 204 includes a sidewall, an outer sheath or tubular member 292 and an internal structural member 294. The outer sheath or tubular member 292 of the inflatable member 204 defines a lumen 293 and the structural member 294 is disposed within the lumen 293.

In the illustrated embodiment, the structural member 294 is porous such that it is configured to allow a fluid to pass through it. In the illustrated embodiment, the structural member 294 defines a series or a plurality of cavities and/or channels 295. The cavities and/or channels 295 are configured to allow passage of fluid through the structural member 294 and thus through the lumen 293 of the tubular member 292. In some embodiments, the structural member includes a sponge-like structure.

In the illustrated embodiment, the inflatable member or cylinder 204 includes a second end portion or tip member 224 and a first end portion or tip member 232. The tip members 224 and 232 are coupled to the end portions of the outer sheath or tubular member 292. In the illustrated embodiment, the structural member 294 is disposed between the tip members 224 and 232.

In some embodiments, the structural member 294 may allow the inflatable member 204 to be inflated at a relatively low pressure. In some embodiments, this may allow the user to inflate the inflatable member 204 with less pumps or activations of the pump or may allow the user to apply less force to the pump to inflate the inflatable member 204. Details of the pump assembly 201 are described below. Additionally, in some embodiments, the structural member 294 of the inflatable member 204 may allow the inflatable member 204 to retain or maintain a tubular shape (or a more anatomically correct shape) when the inflatable member 204 is in its deflated configuration.

In the illustrated embodiment, the outer sheath 292 includes an outer surface 296 that is smooth. In other embodiments, the outer surface 296 includes grooves or ridges or is otherwise not smooth. In the illustrated embodiment, the outer sheath 292 has a thickness T. In some embodiment, the thickness T is less or smaller than a radius of the outer sheath 292.

In some embodiments, the outer sheath 292 is formed or silicone, urethane or a thermoplastic elastomer. In other embodiments, the outer sheath 292 is formed of another biocompatible material. In some embodiments, the structural member 294 is formed of a low durometer silicone, urethane, or a thermoplastic elastomer. In other embodiments, the structural member 294 is formed of another biocompatible material.

The pump assembly 201 may switch between an inflation mode in which the fluid in the reservoir 202 is transferred to the inflatable member 204 (or inflatable members) through the pump assembly 201 in a first direction (e.g., inflation direction) and a deflation mode in which the fluid in the inflatable member 204 (or inflatable members) is transferred back to the reservoir 202 through the pump assembly 201 in a second direction (e.g., deflation direction).

The pump assembly 201 includes a pump bulb member or pump 231, a valve body 233, and a selection member 239. The selection member may be used to select or change the mode in which the pump assembly 201 is in. For example, the selection member 239 may be moved from a first position to a second position to place the device in its deflation mode. The selection member 239 may then be moved back to its first position to place the device in its inflation mode. In some embodiments, the selection member 239 is movable with respect to the valve body 233. For example, the selection member 239 may be slidably coupled or slideable with respect to the valve body 233. In some embodiments, the selection member 239 includes stop members, such as shoulders or detents that engage members of the valve body 233 to lock or help retain the selection member 239 in one of its first and second positions. In other embodiments, the selection member 239 may be disposed or coupled to another portion of the device.

The pump 231 may be squeezed or depressed by the user in order to facilitate the transfer of fluid from the reservoir 202 to the inflatable member 204. For example, in the inflation mode, while the user is operating the pump 231, the pump 231 may receive the fluid from the reservoir 202, and then output the fluid to the inflatable member 204. When the user switches to the deflation mode, at least some of the fluid can automatically be transferred back to the reservoir 202 (due to the difference in pressure from the inflatable member 204 to the reservoir 202). Then, the user may squeeze the inflatable member 204 to facilitate the further transfer of fluid through the pump 231 to the reservoir 202.

Then, when the user wants to deflate the inflatable members 204, the user moves selection member 239 to its deflated position. The user may then operate the pump 231 to deflate the inflatable members 204 (i.e., move the fluid from the inflatable members 204 to the reservoir 202). For example, the user may repeatedly depress or squeeze the pump 231 until the deflation is completed. The pump 231 may then return to its original form, which provides a suction force causing fluid to be drawn into the pump 231 from the inflation members 204. The fluid from the inflation members 204 fills the pump 231 (or at least partially fills the pump 231). This pump cycle is repeated until the inflatable members 204 are deflated.

In some examples, the fluid may automatically (upon movement of the selection member 239 to its deflate position) flow out of the inflation member 204 and into the reservoir 202 without the user depressing or squeezing the pump 231 until the pressure is at least partially equalized between the reservoir 202 and the inflatable member 204.

In some examples, after the inflation member 204 has been deflated, the pump 231 may be squeezed to place the pump in a contracted position or configuration.

Figure 6:
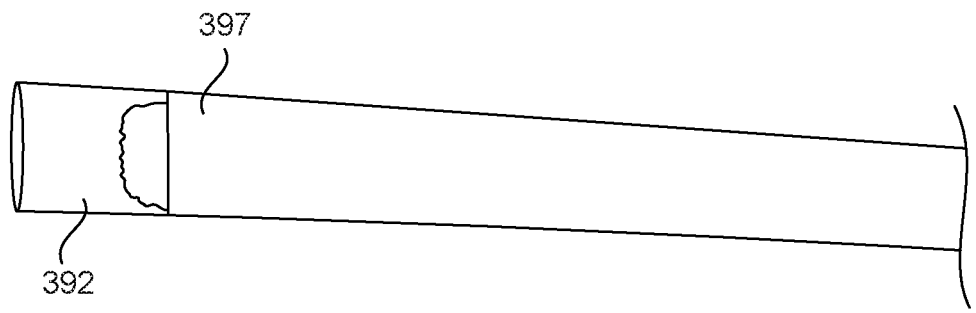
FIGS. 6-10 illustrate cylinder or inflatable member being formed according to an embodiment.
Figure 7:
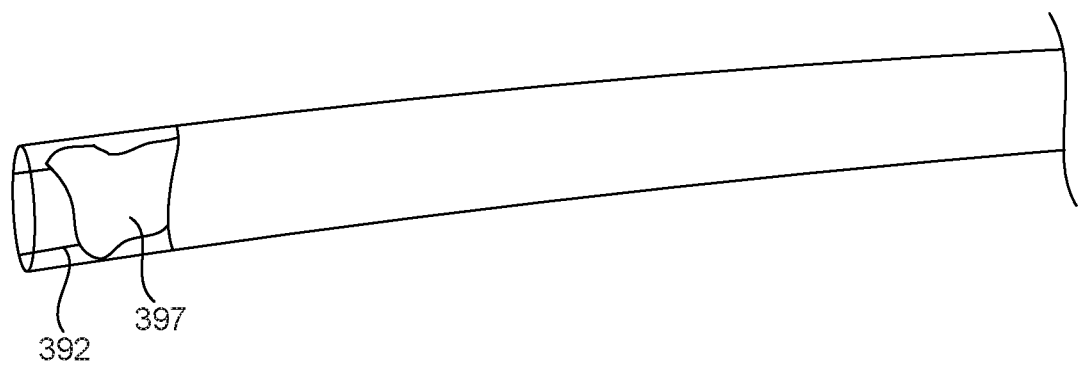

FIGS. 6-10 illustrate cylinder or inflatable member being formed according to an embodiment. FIGS. 6 and 7 illustrate an outer sheath member 392. The outer sheath member 392 is a tubular member that defines a lumen. The lumen is filled or packed with a material. In some embodiments, the lumen is filled with a material that is water-soluble. For example, the lumen may be filled with salt or wax particles. In other embodiments, the lumen is packed or filled with a different water-soluble material. As illustrated in FIG. 6 the sheath member 392 is filled with fine particles of salt 397. As illustrated in FIG. 7, the sheath member 392 is filled with coarse salt particles 399.

Figure 8:
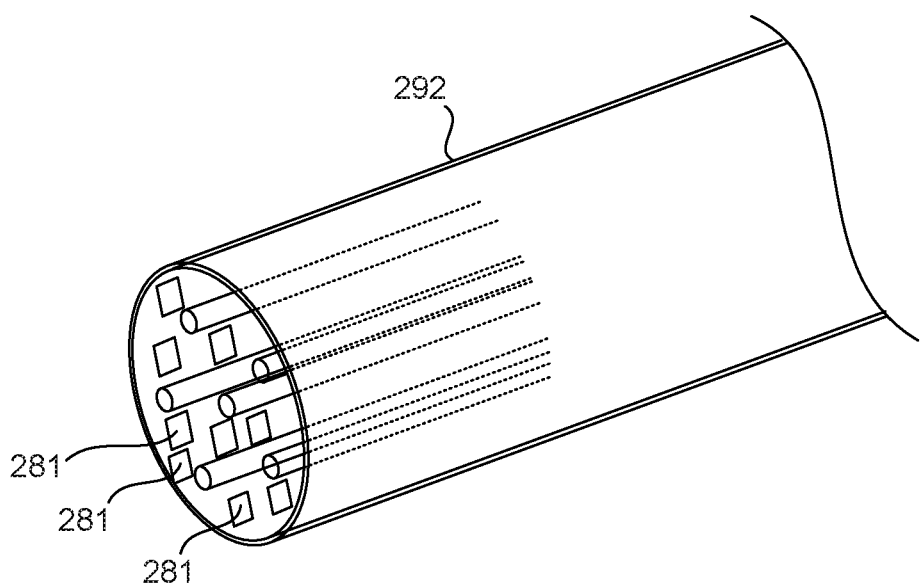
Figure 9:
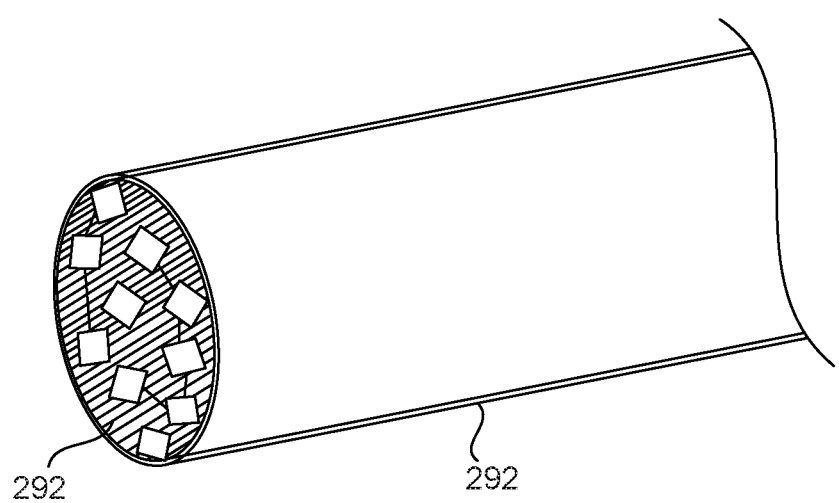

In some embodiments, once the lumen is filled with the water-soluble material, elongate members 281 are inserted into the lumen. As illustrated in FIG. 8, a plurality of elongate members 281 are inserted into the lumen such that the elongate members extend along or in the same direction as the longitudinal axis of the sheath 292. The elongate members 281 are surrounded by the water-soluble material (such as the salt). In some embodiments, the elongate members 281 facilitate the removal of the salt. Specifically, after the elongate members 281 are disposed within the lumen, the material of the structural member may be injected or inserted into the lumen. Once the material of the structural member has hardened, the elongate members 281 can be removed from the lumen. Water or another fluid, can then be passed through the lumen, including through the spaces or channels where the elongate members 281 were located. As the water passes through the lumen, the water-soluble material will also exit the lumen, leaving just the structural member disposed within the lumen. FIG. 9 is a perspective view of the sheath member 292 and the structural member 294 disposed within the lumen of the sheath member 292.

Figure 10:
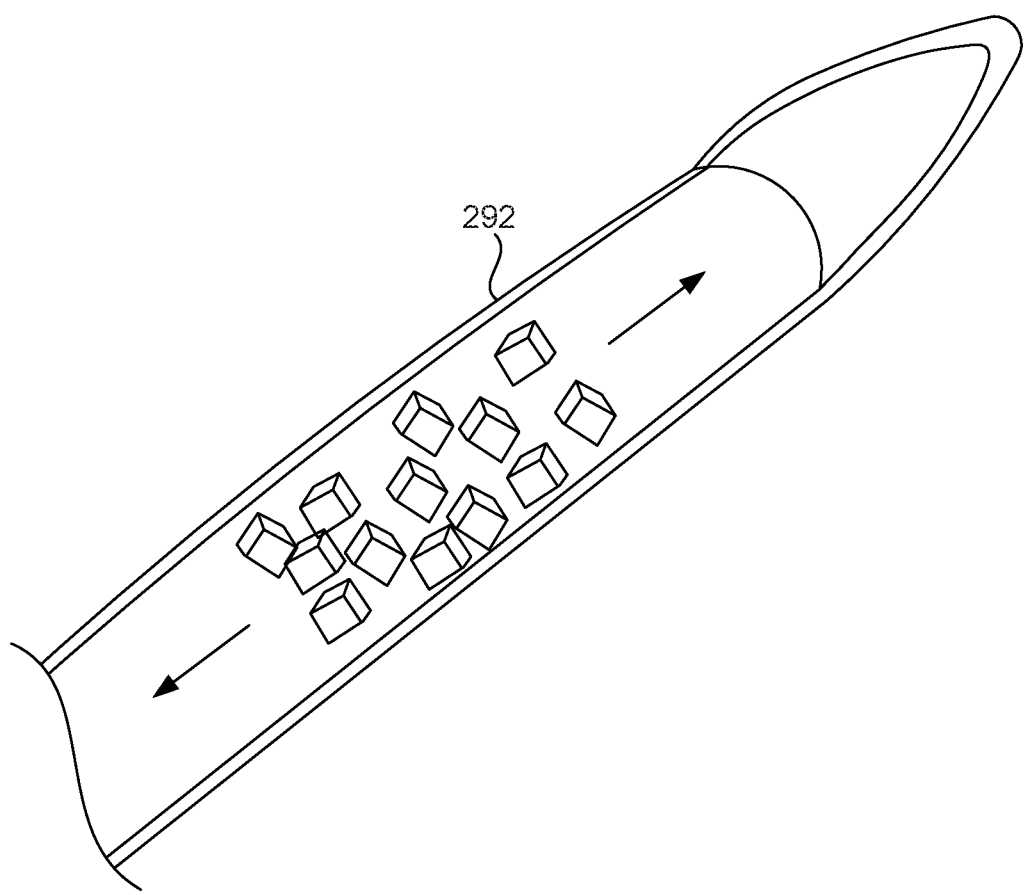

FIG. 10 is a cross-sectional view of the outer sheath 292 with salt crystals disposed within the lumen of the outer sheath 292.

Figure 11:
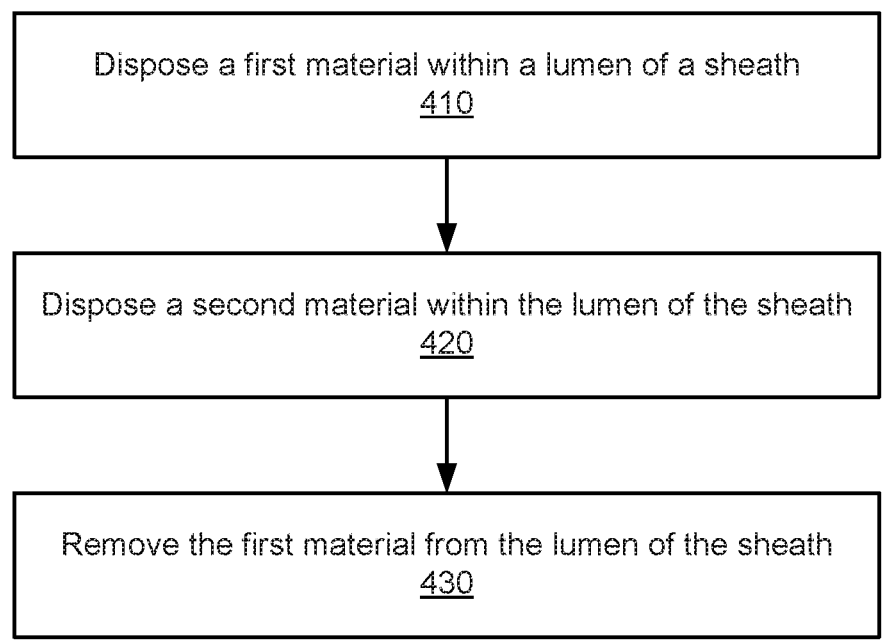
FIG. 11 is a flow chart of a method of making a cylinder or inflatable member of a penile prosthesis according to an embodiment.

FIG. 11 is a flow chart of a method 400 of forming an inflatable member according to an embodiment. At 410, a first material is disposed within a lumen of a sheath or elongate member. At 420, a second material is disposed within the lumen of the sheath or elongate member. In some embodiments, the second material is different than the first material. In some embodiments, the first material is a water-soluble material. At 430, the first material is removed from the lumen. In some embodiments, the second material remains within the lumen after the first material is removed.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. An implant, comprising:
   an inflatable member, the inflatable member having an outer sheath including a sidewall, the sidewall having an outer surface and an inner surface that defines a lumen, the inflatable member including a porous structure disposed within the lumen;
   an end cap coupled to a first end portion of the sidewall and defining a lumen, the porous structure being disposed within the lumen defined by the end cap; and
   a pump assembly configured to facilitate a transfer of a fluid from a reservoir to the lumen of the inflatable member to place the inflatable member in an inflated configuration.

2. The implant of claim 1, wherein the porous structure defines a plurality of cavities.

3. The implant of claim 1, wherein the inflatable member defines a longitudinal axis, the porous structure extends along the longitudinal axis.

4. The implant of claim 1, wherein the outer surface of the sidewall is substantially smooth.

5. The implant of claim 1, wherein the inflatable member is configured to be placed in an inflated configuration and a deflated configuration.

6. The implant of claim 1, wherein the inflatable member is configured to be placed in an inflated configuration and a deflated configuration, the inflatable member having a tubular shape when in the deflated configuration.

7. The implant of claim 1, wherein the inflatable member is configured to be placed in an inflated configuration and a deflated configuration, the inflatable member having a tubular shape when in the inflated configuration.

8. The implant of claim 1, wherein the inflatable member is configured to be placed in an inflated configuration and a deflated configuration, the inflatable member having a tubular shape when in the deflated configuration and having a tubular shape when in the inflated configuration.

9. The implant of claim 1, wherein the inflatable member is configured to be placed in an inflated configuration and a deflated configuration, the inflatable member configured to extend along a longitudinal axis of the inflatable member when placed in the inflated configuration.

10. The implant of claim 1, wherein the inflatable member is configured to be placed in an inflated configuration and a deflated configuration, the inflatable member configured to extend in a direction transverse to a longitudinal axis of the inflatable member when placed in the inflated configuration.

11. The implant of claim 1, wherein the porous structure defines a plurality of cavities, the fluid being configured to be disposed within the plurality of cavities when the inflatable member is placed in an inflated configuration.

12. The implant of claim 1, wherein the end cap is a first end cap and the first cap is coupled to the first end portion of the sidewall such that a portion of the first cap is disposed within the lumen defined by the inner surface of the inflatable member, the implant further comprising:
    a second cap coupled to a second end portion of the sidewall.

13. The implant of claim 1, wherein the end cap is a first end cap, the implant further comprising:
    a second cap coupled to a second end portion of the sidewall.

14. The implant of claim 1, further comprising:
    a reservoir configured to retain the fluid, wherein the pump is configured to help facilitate a transfer of the fluid from the reservoir to the inflatable member when the implant is in an inflation mode.

15. The implant of claim 1, wherein the pump assembly includes a valve body and a pump bulb member.

16. A method of forming an inflatable member of an implant, comprising:
disposing a first material within a lumen of a sheath;
inserting tubular members within the lumen of the sheath;
after inserting the tubular members within the lumen of the sheath, disposing a second material within the lumen of the sheath, the second material being different than the first material;
removing the tubular members from the lumen of the sheath; and
removing the first material from with lumen of the sheath while leaving the second material disposed within the sheath.

17. The method of claim 16, wherein the first material is water-soluble, the second material is non-soluble in water.

18. The method of claim 16, wherein the removing the first material from the lumen includes passing a liquid through the lumen of the sheath.

19. The method of claim 16, wherein the second material is disposed within the lumen of the sheath after the first material is disposed within the sheath.

20. The implant of claim 1, wherein the outer sheath is an outermost sheath of the inflatable member.

\* \* \* \* \*